US00PP31412P2

(12) United States Plant Patent
Hansen

(10) Patent No.: US PP31,412 P2
(45) Date of Patent: Jan. 28, 2020

(54) ***ACHILLEA* PLANT NAMED 'SASSY SUMMER SUNSET'**

(50) Latin Name: ***Achillea* hybrid**
Varietal Denomination: Sassy Summer Sunset

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,798

(22) Filed: Jan. 14, 2019

(51) Int. Cl.
*A01H 5/02* (2018.01)
*A01H 6/14* (2018.01)

(52) U.S. Cl.
USPC ..... Plt./263.1

(58) Field of Classification Search
USPC ..... Plt./263.1

CPC ..... A01H 5/02; A01H 5/025; A01H 5/0205; A01H 6/14; A01H 6/04
See application file for complete search history.

(56) References Cited

PUBLICATIONS

Germania Seed 2018 Walters Gardens Bare Root and Plug Perennials, retrieved on Sep. 23, 2019, retrieved from the Internet at https://www.germaniaseed.com/pdf/2019/749_walters.pdf, pp. 1,24. (Year: 2018).*
Walters Gardens, Inc. 2018 Summer Selections Price List & Order Forms, retrieved on Sep. 23, 2019, retrieved from the Internet at https://wgi-img.s3.amazonaws.com/cms/4838023d0a27c4d7d4ba5d7765922912.pdf, pp. 1-4. (Year: 2018).*

* cited by examiner

*Primary Examiner* — June Hwu

(57) ABSTRACT

The new and distinct Yarrow, *Achillea* plant named 'Sassy Summer Sunset', with narrow, silvery, fern-like foliage; tall, stiff, heavily branched peduncles with dark orange inflorescences that mature to yellow, beginning in late June and continuing for about four weeks. The new plant is useful for landscaping, as a specimen or en masse and as a cut flower.

1 Drawing Sheet

Botanical designation: *Achillea* hybrid.
Cultivar denomination: 'Sassy Summer Sunset'.

STATEMENT REGARDING PRIOR DISCLOSURES UNDER 37 CFR 1.77(B)(6)

The first public disclosure of the claimed plant, in the form of a sale, was made by Walters Gardens, Inc. on Jul. 9, 2018. Prior to that, on Feb. 1, 2018 the claimed plant was displayed as a photograph with a brief description on a website operated by Walters Gardens, Inc., who obtained the plant and all information relating thereto, from the inventor. No plants of *Achillea* 'Sassy Summer Sunset' have been sold, in this country or anywhere in the world, nor has any disclosure of the new plant been made, more than one year prior the filing date of this application, and such sale or disclosure within one year was either derived directly or indirectly from the inventor.

BACKGROUND OF THE PLANT

The present invention relates to the new and distinct yarrow herein also referred to as *Achillea* 'Sassy Summer Sunset', by the cultivar name, 'Sassy Summer Sunset', or as the new plant. The new plant was selected by the inventor as a single seedling resulting from a cross in an isolation block between a proprietary unreleased plant identified with the breeder code 13-5-6 (not patented) crossed with siblings of 13-5-6 in research facility of a wholesale perennial grower based in Zeeland, Mich., USA. The seeds from this cross were collected on Sep. 23, 2014. The single seedling was then isolated and compared in subsequent years to other Yarrow and subsequently found to be different from all cultivars known to the discoverer and eventually given the breeder code 14-17-4.

Asexual propagation at the same nursery in Zeeland, Mich., USA by shoot tip cuttings and division has shown 'Sassy Summer Sunset' to be stable and reproduce true to type in successive generations.

SUMMARY OF THE PLANT

*Achillea* 'Sassy Summer Sunset' has not been observed in all possible environmental conditions. The phenotype may vary slightly with changes in environments such as light intensity, fertility, water availability, etc. without, however any variation in genotype.

*Achillea* 'Sassy Summer Sunset' is distinct from all cultivars known to the inventor in the following traits:

1. Narrow, silvery, fern-like foliage with medium tall height and dense upright habit.
2. Numerous large panicles of dark orange inflorescences that mature to yellow.
3. Heavily-branched peduncles with center main cluster to about 18 cm across.
4. Sturdy stems withstand wind and rain.
5. Long flowering period beginning late June and continuing for about four weeks.

Plants of *Achillea* 'Sassy Summer Sunset' are most similar to 'Strawberry Seduction' U.S. Plant Pat. No. 18,401, 'Terracotta' (not patented) and 'Red Beauty' (not patented). 'Red Beauty' is taller in habit, has less stiff stems and the flowers are reddish pink. 'Strawberry Seduction' has more lax flower stems, the foliage is less silvery-glaucous and not as thick in substance, the flower stems have less branching and the flowers are a different color. 'Terracotta' has a larger and much looser habit. Plants and photographs of the parent varieties have not been maintained and no comparison between the parents and new plant are possible.

BRIEF DESCRIPTION OF THE DRAWINGS

The color drawings illustrate the overall characteristics of *Achillea* 'Sassy Summer Sunset' as a three-year-old plant in a full-sun trial garden in Zeeland, Mich. The colors are as true as reasonably possible given the technology available. The color values may vary slightly depending on light intensity and quality.

DETAILED BOTANICAL DESCRIPTION

Figure 1:
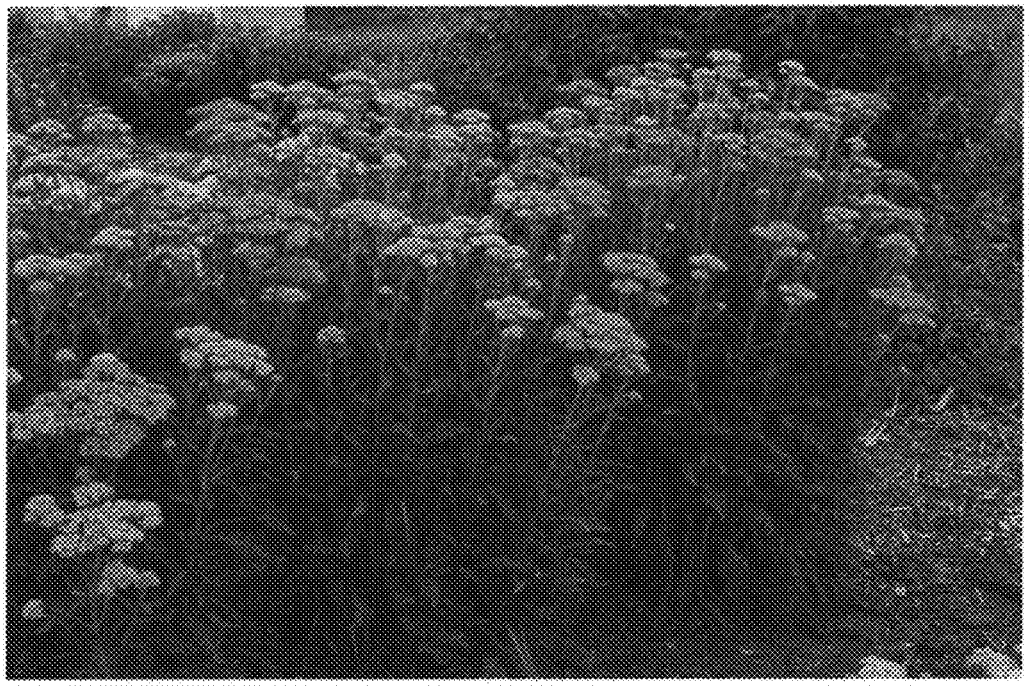
FIG. 1 shows the new plant in a trial facility.
Figure 2:
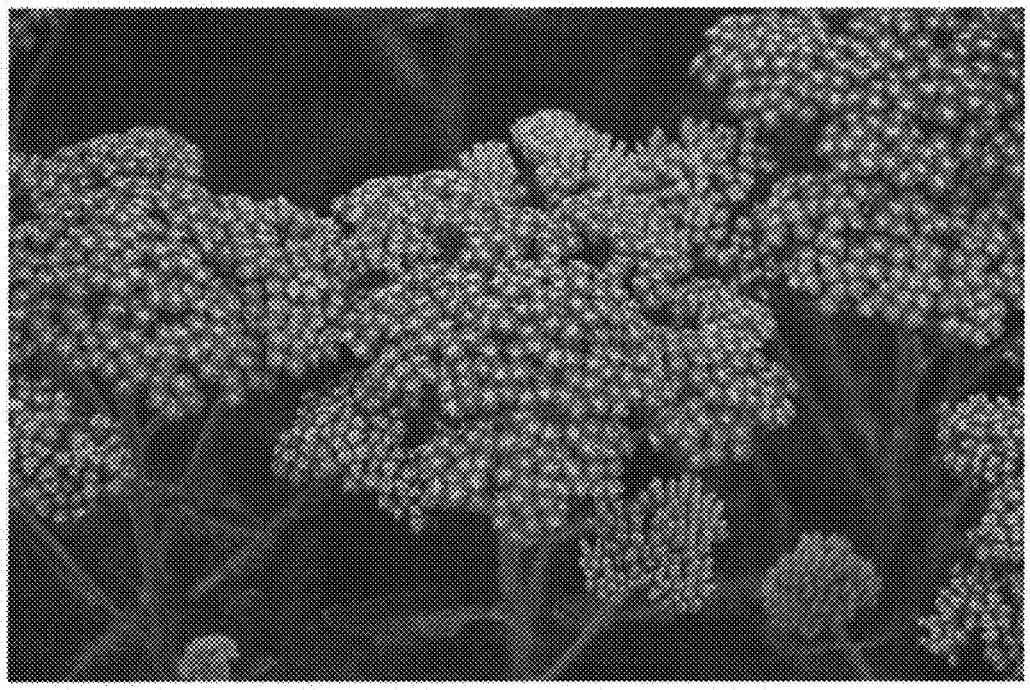
FIG. 2 shows a close-up of the flowers of the new plant.

The following description is based on a three-year-old plant growing in a full-sun trial garden in Zeeland, Mich., USA. Environmental conditions for the growing season daytime temperatures range between 12-30° C., and night temperatures range between 6-19° C. Except for ordinary dictionary color usage, color references are according to The Royal Horticultural Society Colour Chart, 2015 edition.

Parentage: Female or seed parent 13-5-6 is comprising a cross between *Achillea millefolium* 'Strawberry Seduction' U.S. Plant Pat. No. 18,401 x *sibirica*; male or pollen parent sibling of 13-5-6;

Asexual propagation: Shoot tip cuttings, about 10 to 14 days to initiate roots; time to finish as # 1 field grown size about 9 months;

Plant habit: Dense axillary branches; upright, heavily-branched, herbaceous, winter-hardy, perennial mound; up to 40.0 cm tall and 82.0 cm wide; average about 38.0 cm tall and about 65.0 cm across;

Leaves: Alternate; glabrous; pinnatisect with lobules moderately incised; lanceolate; acute apex; base attenuate; sessile except proximal leaves; lanulose abaxial and adaxial; up to 39.0 cm long and 8.0 cm wide with individual lobes to 14.0 mm wide and 3.2 cm long, average about 14.2 cm long and 4.0 cm wide;

Leaf color: Young expanding leaves adaxial blend between RHS 189B and RHS N138D and abaxial blend between RHS 189B and RHS N138C; mature leaves adaxial nearest RHS N138B, abaxial nearest RHS N138C;

Veins: Pinnate; only abaxial midrib obvious;

Midrib color: Adaxial nearest RHS 192C and abaxial nearest RHS 192C;

Petiole: Channeled; lanulose; to 4.0 cm long and 5.0 mm wide at base; color nearest RHS 193D;

Stems: Upright; cylindrical; lanulose to tomentulose; color mature stems nearest RHS 146C, young stems nearest RHS N138D;

Inflorescence: Radiate; composite consisting of about five ray and about twelve disk florets; on heavily branched terminal stems; individual inflorescence about 4.5 mm diameter, about 4.5 mm tall from bottom of involucral bracts to top of exserted stigmas; disk about 2.0 mm across; attitude mostly upright; producing branched stems with about 400 inflorescences per stem;

Receptacle: About 3.0 mm tall; color nearest RHS 148C;

Inflorescence fragrance: Not detected;

Phyllaries: About ten in two whorls; lanceolate; acute apex; truncate base; margin entire; outer or lower set about 2.0 mm long and 1.0 mm across, inner set about 3.0 mm long and 1.0 mm across; glabrous adaxial, pubescent abaxial; tightly adpressed against ray petals;

Phyllary color: Lower set between RHS 147B and RHS 147C adaxial and abaxial, upper set nearest RHS 147B adaxial and abaxial;

Flowering period: Late June, for about 4 weeks;

Flower longevity: 4 to 6 days;

Inflorescence buds: With ray florets still erect 5.0 mm tall and 2.0 mm across; ovoid;

Inflorescence bud color: Ray florets while still upright exposed petal color nearest RHS 42A distally and nearest RHS NN155C just above phyllaries; phyllaries color nearest RHS 147C;

Peduncle: Cylindrical; lanulose to tomentulose; strong; upright attitude; heavily branched; up to 7.0 mm diameter at base, average 5.0 mm diameter; and 36.0 cm long, flowering in upper 8.0 cm; branches to about 14.0 cm long and 5.0 mm diameter at base;

Peduncle color: Between RHS 189A and RHS 189B;

*Ray florets*.—Imperfect; staminate; typically about five per inflorescence; containing only gynoecium with style about 2.5 mm long and split stigma.

*Ray floret ligule*.—Rounded with basal claw; apex rounded to slightly emarginate, margin entire; base claw, attenuate; opening to a 90° angle; glabrous adaxial and adaxial; about 4.0 mm long and about 5.0 mm wide; basal claw about 1.5 mm long and about 0.5 mm across.

*Young ray floret ligule color when first flat*.—Adaxial nearest RHS N34A, abaxial nearest RHS 42D and base nearest RHS NN155C.

*Mature ray floret ligule color*.—Adaxial nearest RHS 20B; abaxial nearest RHS 161D.

*Ray floret ligule color before dehiscing*.—Adaxial nearest RHS 161D with blush of nearest RHS 20B; abaxial nearest RHS 161D.

*Style*.—Cylindrical; about 2.0 mm long and 0.2 mm diameter; exserted; color nearest RHS 23D.

*Stigma*.—Bifid; about 1.5 mm long and 0.2 mm diameter; color nearest RHS 23D.

Disk florets: About twelve per capitulum; tubular; glabrous; consisting of tepals, staminal tube and pistil; size about 3.5 mm long by 1.0 mm wide at apex;

*Tepals*.—Five; 2.5 mm long and 0.7 mm wide, fused in the basal 2.0 mm, acute apex.

*Tepal color*.—Nearest RHS 23D.

*Staminal tube*.—Made up of five adnate stamens; about 2.0 mm long.

*Filaments*.—Cylindrical; about 0.7 mm long and 0.1 mm diameter; color nearest RHS NN155A.

*Anther*.—About 1.0 mm long; color nearest RHS 17B.

*Pollen*.—Fine, round, closest to RHS 17B.

*Style*.—Bifid; cylindrical; exserted; about 2.0 mm long and 0.2 mm diameter; color nearest RHS 23D.

*Stigma*.—Bifid; reflexing as it matures; about 1.5 mm long; color nearest RHS 23D.

Seed: Flattened deltoid; acute apex and truncate base; surface glabrous; about 2.0 mm long and 0.7 mm across base;

Seed color: Between RHS 165A and RHS 165B in center and RHS 161D around edges;

*Achillea* 'Sassy Summer Sunset' is tolerant of winter temperatures as low as −35° C. and summer temperatures as high as 38° C. It is not known to be tolerant of diseases and pest that are common to other *Achillea* cultivars.

I claim:

1. The new and distinct cultivar of *Achillea* plant named 'Sassy Summer Sunset' as described and illustrated.

* * * * *